(12) United States Patent
Chen et al.

(10) Patent No.: US 7,501,554 B2
(45) Date of Patent: Mar. 10, 2009

(54) TRANSGENIC ANIMALS PRODUCING LOW-LACTOSE MILK AND NEWLY IDENTIFIED HUMAN SMALL INTESTINAL EXTRACELLULAR LACTASE-PHLORIZIN HYDROLASE (ECLPH) GENE

(75) Inventors: Chuan-Mu Chen, Taichung (TW); Winston T. K. Cheng, Taipei (TW); Hsiao-Ling Chen, Taipei (TW)

(73) Assignee: National Chung Hsing University, Taichung (TW)

( * ) Notice: Subject to any disclaimer, the term of this patent is extended or adjusted under 35 U.S.C. 154(b) by 0 days.

(21) Appl. No.: 11/434,332

(22) Filed: May 15, 2006

(65) Prior Publication Data

US 2007/0266451 A1    Nov. 15, 2007

(51) Int. Cl.
*A01K 67/027* (2006.01)
*C12N 15/00* (2006.01)

(52) U.S. Cl. .............................. 800/14; 800/25; 800/15; 800/16; 800/18

(58) Field of Classification Search .................. 800/14, 800/25, 15, 16, 18
See application file for complete search history.

(56) References Cited

U.S. PATENT DOCUMENTS 5,907,080 A * 5/1999 Karatzas et al. ............... 800/25

OTHER PUBLICATIONS

Bowie, et al. Science, 247: 1306-10, 1990.*
Skolnick et al. TibTech 18:34-39, 2000.*

* cited by examiner

*Primary Examiner*—Anne Marie S Wehbe
*Assistant Examiner*—Fereydoun G. Sajjadi
(74) *Attorney, Agent, or Firm*—Panitch Schwarze Belisario & Nadel LLP

(57) ABSTRACT

The invention provides a transgenic animal producing low-lactose milk, which is transformed with a gene encoding an extracellular lactase-hydrolyzing enzyme cloned from a human small intestinal cDNA library. The invention also provides a new extracellular lactase-phlorizin hydrolase (ecLPH) gene that can express human lactase-hydrolyzing enzyme in the mammary gland of animals. The invention can be used in the production of low-lactose milk.

9 Claims, 3 Drawing Sheets
(3 of 3 Drawing Sheet(s) Filed in Color)

Fig 1
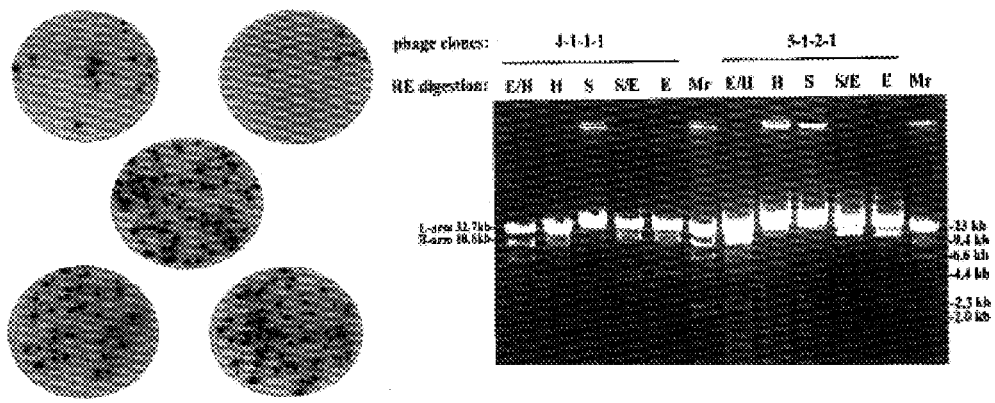
Fig 2
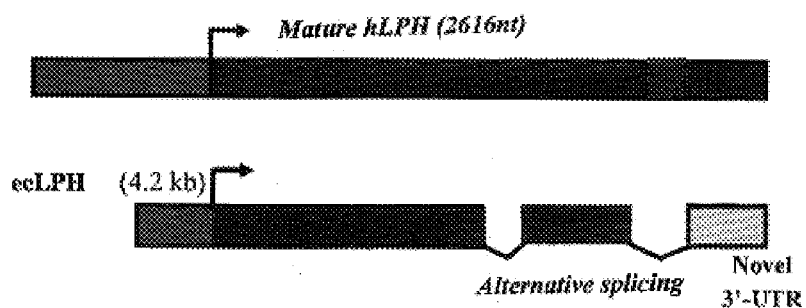
Fig 3A
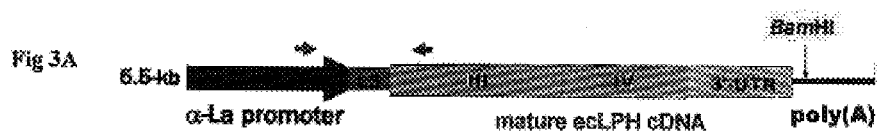
Fig 3B
Fig 3C
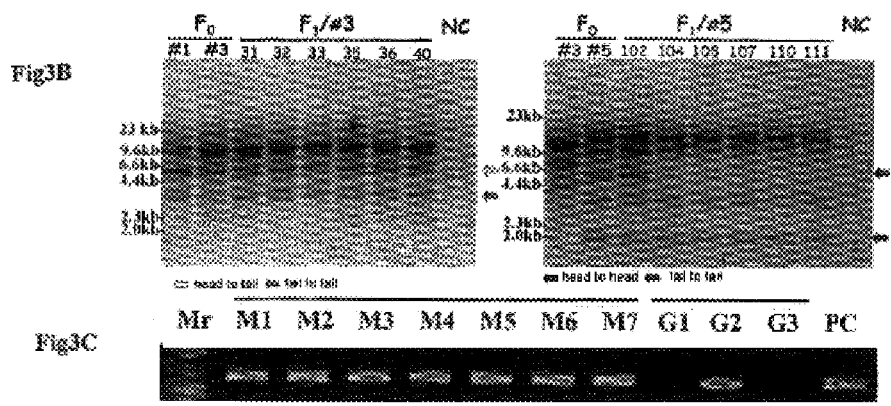

(A) Heterozygote mouse (ecLPH +/-)  (B) Homozygote mouse (ecLPH +/+)  (C) Control mouse (LPH-/-)

(A) LPH-Tg mammary tissue  (B) ecLPH-Tg mammary tissue  (C) Non-Tg mammary tissue

TRANSGENIC ANIMALS PRODUCING LOW-LACTOSE MILK AND NEWLY IDENTIFIED HUMAN SMALL INTESTINAL EXTRACELLULAR LACTASE-PHLORIZIN HYDROLASE (ECLPH) GENE

FIELD OF THE INVENTION

The present invention relates to the biotechnical field of gene cloning and transgenic animals, which utilizes a genetic cloning technique involving the human genomic library, and development of mammary gland-specific expression vectors to provide a platform technology of transgenic animals producing low-lactose milk. More specifically, the present invention also provides a new extracellular lactase-phlorizin hydrolase (ecLPH) gene, which can be used to transform animals to produce low-lactose milk.

BACKGROUND OF THE INVENTION

Milk is a food source of high nutrition value, which is rich in proteins, vitamins, carbohydrates, calcium and other minerals. Except for being utilized as the nutrition source for newborn babies and infants, it can also be used to prevent osteoporosis in older people, and especially elderly people. Lactose is the major carbohydrate in milk. However, people with lactose intolerance cannot decompose the abundant lactose in milk, which is caused by reduction in the activity of lactase-phlorizin hydrolase. Un-decomposed lactose accumulates in the intestine and induces bacterial fermentation, producing carbon dioxide, hydrogen and methane and resulting in symptoms such as abdominal distension, nausea and diarrhea. Such disadvantages limit the use of milk and dairy products including milk or lactose.

The best strategy to treat patients suffering from lactose intolerance syndrome or to prevent the syndrome, is to avoid the ingestion of dairy products containing large amounts of lactose. However, many people, including lactose-intolerant people, enjoy dairy products containing milk or otherwise containing lactose. Therefore, the development of low-lactose milk and other dairy products containing lactose is crucial. It is now known that α-lactalbumin is an abundant calcium metalloprotein in milk. The binding between α-lactalbumin and galactosyltransferase in the Golgi body can modify the specificity of the galactosyltransferase by forming the lactose synthetase binary complex to synthesize lactose. In order to understand the effect of α-lactalbumin on lactogenesis and the relationship between α-lactalbumin and lactose, Stinnakre et al. utilized gene targeting in embryonic stem cells to produce transgenic mice with heterozygous or homozygous deficiencies in the α-lactalbumin gene. They found that the milk of the transgenic mice with homozygous deficiencies in the α-lactalbumin gene lacked not only α-lactalbumin but also lactose. However, the lack of lactose resulted in highly viscous milk since lactose is an important regulator of osmotic pressure during lactation, and thus the female mice cannot feed their pups smoothly. In the milk of the transgenic mice with heterozygous deficiencies in the α-lactalbumin gene, α-lactalbumin decreased by 40% while lactose decreased by 10-20% (Stinnakre, M. G., Vilotte, J. L., Soulier, S. and Mercier, J. C., 1994. Creation and phenotype analysis of α-lactalbumin—deficient mice. Proc. Natl. Acad. Sci. 91: 6544-6548).

In 1996, L'Huillier et al. created a construct wherein a ribozyme 5 (RZ5) gene is downstream of the mouse mammary tumor virus (MMTV) long terminal repeat (LTR) so that the RZ5 gene can be specifically expressed in mammary gland cells. Utilizing gene-transformation technology, transgenic mice highly expressing the RZ5 gene in their mammary glands were developed. RZ5 can specifically degrade α-lactalbumin mRNA to reduce the production of α-lactalbumin and further affects the production of lactose (L'Huillier, P. J., Soulier, S., Stinnakre, M. G., Lepourry, L., Davis, S. R., Mercier, J. C. and Vilotte, J. L., 1996. Efficient and specific ribozyme-mediated reduction of bovine alpha-lactalbumin expression in double transgenic mice. Proc. Natl. Acad. Sci. 93: 6698-6703). According to the studies of Berns and Hauswirth (1979), adeno-associated virus (AAV), which is tissue-specific, uses cells in the tissues of human respiratory and gastrointestinal systems as host cells. Moreover, since AAV is resistant to high temperature and low pH, it is potentially resistant to oral administration (Bern, K. I. and Hauswirth, W. W., 1979. Adeno-associated viruses. Adv. Virus. Res. 25: 407-409). In 1998, During et al. reconstructed AAV into a vector, wherein most of the AAV genes were deleted and only 145 bp of terminal repeats were retained. The resulting AAV vector contains few viral genes so that the possibilities of gene recombination and viral gene expression were reduced to minimum. Then a β-galactosidase gene was constructed onto the AAV vector, and the vector was fed to rats through oral administration. It is found that the β-galactosidase gene was highly expressed at the 6th hour post feeding, and the expression was sustained and stable through 6 months (During, M. J., Xu, R., Young, D., Kaplitt, M. G., Sherwin, R. S, and Leone, P., 1998. Peroral gene therapy of lactose intolerance using an adeno-associated virus vector. Nature Medicine 4: 1131-1135).

Even in view of the aforementioned studies, acceptable low-lactose milk has not been developed. In one aspect, the normal osmotic pressure of lactation is affected. In another aspect, the use of viral vectors has potential danger. Therefore, the development of a new technique for producing low-lactose milk and other dairy products containing lactose is necessary. The present invention satisfies this necessity.

BRIEF SUMMARY OF THE INVENTION

One aspect of the present invention relates to a transgenic animal producing low-lactose milk, which is transformed with a gene encoding an extracellular lactase-hydrolyzing enzyme, wherein the gene is cloned from a human small intestinal cDNA library. Preferably, the gene is a gene encoding an extracellular lactase-phlorizin hydrolase (ecLPH).

Another aspect of the present invention relates to an isolated new extracellular lactase-phlorizin hydrolase gene cloned from a human small intestinal cDNA library that can be expressed with a mammary gland-specific expression vector.

A further aspect of the present invention relates to a heterologous gene expression vector construct, comprising the extracellular lactase-phlorizin hydrolase (ecLPH) gene of the present invention constructed in a mammary gland-specific expression vector which can be expressed in a mammary gland.

Yet another aspect of the present invention relates to an isolated extracellular lactase-phlorizin hydrolase gene cloned from a human small intestinal cDNA library that can be expressed with a mammary gland-specific expression vector, encoding an extracellular protein without a membrane-binding domain, the gene lacking Exon 12 and Exon 15-17 compared with a known human lactase-phlorizin hydrolase (hLPH) gene.

A still further aspect of the present invention relates to a method for producing low-lactose milk, wherein the heterologous gene expression vector construct of the present invention is introduced into a pronucleus to produce a transgenic animal, which produces low-lactose milk to benefit the large group of people suffering from lactose intolerance syndrome.

Another aspect of the present invention relates to a heterologous gene expression vector construct comprising the gene of the present invention that can be expressed with a mammary gland-specific expression vector, and (1) a promoter 5'-regulatory sequence, which is specific for expression in mammary gland epithelial cells and can regulate the heterologous gene so that the gene is continuously and stably expressed during a lactation period of a transgenic mammal; (2) a mammary gland-specific extracellular signal peptide sequence, which can guide the heterologous proteins expressed in the mammary gland epithelial cells of the transgenic mammal so that the proteins are efficiently secreted into milk produced by the transgenic mammal; (3) a heterologous gene, which is downstream of and regulated by the 5'-regulatory sequence and the extracellular signal peptide sequence; and (4) a 3'-regulatory sequence, which is downstream of the coding sequence of the heterologous gene, comprising a polyadenylation signal sequence for stability and integrity of an mRNA molecule transcribed from the heterologous gene and post-transcriptional modification.

A further aspect of the present invention relates to a method for producing low-lactose milk, comprising providing the transgenic animal of the present invention, and obtaining the low-lactose milk from the transgenic animal.

Another aspect of the present invention relates to a method for increasing the growth rate and weight gain of a newborn animal, comprising providing a maternal milk-producing animal and transforming the animal by introducing into the animal the extracellular lactase-phlorizin hydrolase gene of the present invention, and feeding the newborn animal with milk secreted by the maternal animal after pregnancy and delivery of the newborn animal.

Still another aspect of the present invention relates to a method for producing a transgenic animal that produces low-lactose milk, comprising providing a milk-producing animal and transforming the animal by introducing into the animal a gene encoding an extracellular lactase-hydrolyzing enzyme cloned from a human small intestinal cDNA library.

As used herein, the singular forms "a", "an", and "the" include plural referents unless the context clearly indicates otherwise.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

Figure 4:
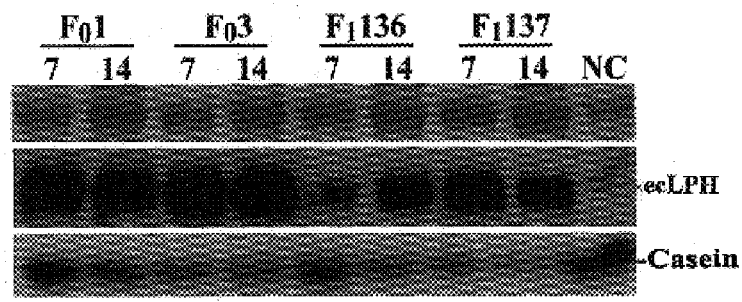

FIG. 1 shows the results obtained by screening the human small intestine 5'-stretch cDNA library for the newly cloned extracellular lactase-phlorizin hydrolase (ecLPH) gene of the present invention. The left part of the drawing shows colonies of the cDNA phage clones obtained after three rounds of screening. The right part of the drawing is the restriction digestion map of the ecLPH phage clones.

FIG. 2 shows the cDNA structure of the newly cloned extracellular lactase-phlorizin hydrolase (ecLPH) gene of the present invention (bottom panel) compared to the known human lactase-phlorizin hydrolase (hLPH) gene (top panel). The hLPH-encoded protein containing a secretion signal peptide in the N-terminus (initial red box region in the top panel) and a transmembrane domain (green box region in the top panel) has been reported as a membrane-anchored protein in the intestinal epithelia. However, the newly identified human ecLPH cDNA structure contains an alternative splicing in the transmembrane domain of hLPH and a novel 3'-UTR sequence (yellow box region in the bottom panel). This clone was examined as a feature of the membrane-anchorless extracellular protein in the present invention.

FIGS. 3A-3C show the results obtained by examining the ecLPH genes in the genomes of the transgenic mice and dairy goats of the present invention. FIG. 3A is a map of the transgene construct. FIG. 3B shows the results of Southern blot analysis of the transgenic mouse genomes of different lines in transgenic founder ($F_0$) and their offsprings ($F_1$) (transgenic line #3 is shown in left blot and transgenic line #5 is shown in right blot), which prove that the heterologous ecLPH gene has indeed been inserted into the chromosomes of transgenic animals. FIG. 3C shows the result of express PCR analysis of the transgenic mice (M1-M7) and transgenic goats (G1-G3).

FIG. 4 shows the result of Western blot analysis of the ecLPH proteins secreted in the milk of the transgenic animals of the present invention. Milk of transgenic mice and normal mice was diluted 20-fold and centrifuged to remove milk lipid. SDS-PAGE and Western blot analysis were performed.

FIGS. 5A-5C show immuno-histochemistry staining of mammary gland tissue sections of the ecLPH transgenic mice of the present invention. Immuno-histochemistry staining was performed to the mammary gland tissues of transgenic mice (A and B) and normal mice (C) with monoclonal antibodies specific for LPH protein. Mammary-gland tissues were taken on the 14$^{th}$ day of the lactation period. Antibody staining analysis showed that homozygous transgenic female mice (B) expressed more ecLPH proteins than heterozygous ones (A).

Figure 6:
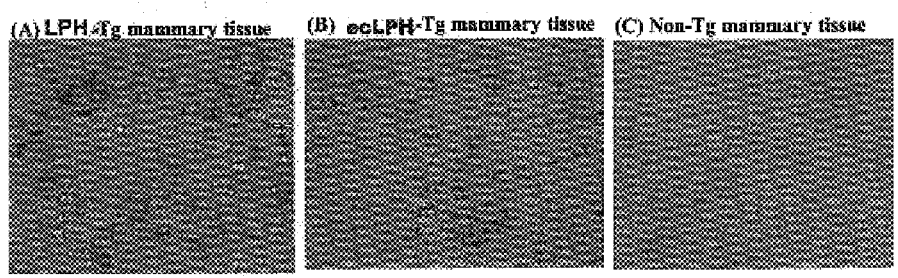

FIGS. 6A-6C show X-Fuc activity staining of the mammary-gland freeze sections of transgenic mice and normal mice during the lactation period. Transgenic female mice and normal female mice were sacrificed on the 14$^{th}$ day of their lactation period, and their mammary-gland tissues were taken for sectioning. Activity staining was performed on the mammary-gland sections of the transgenic mice (FIG. 6A and FIG. 6B) and normal mice (FIG. 6C) with the X-Fuc chromogen. The results showed that both LPH and ecLPH of the transgenic mice were active. Also, the ecLPH appearing in the activity-stained sections of FIG. 6B proved its extracellular property.

Figure 7A:
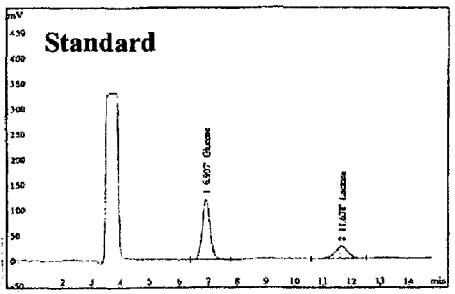
Figure 7B:
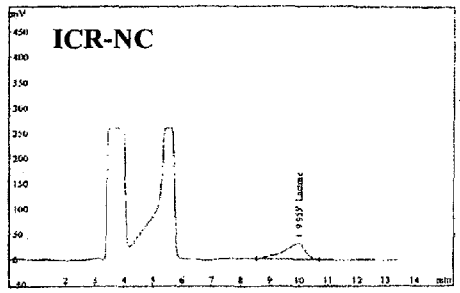
Figure 7C:
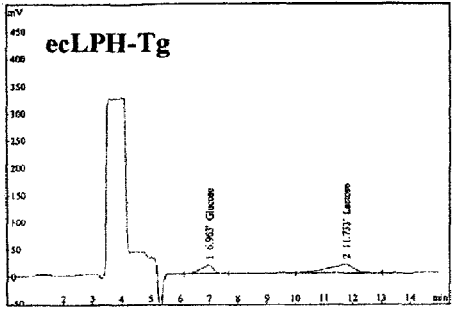
Figure 7D:
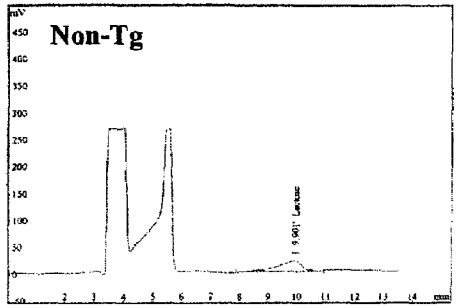

FIGS. 7A-7D show the results obtained by examining the lactose-degrading ability of the human ecLPH enzyme, which was expressed from the mammary gland-specific expression vector of the present invention and secreted into the milk of the transgenic animals during lactation. FIG. 7A shows standard samples of glucose, the monosaccharide molecule, and lactose, the disaccharide molecule, established by HPLC. FIG. 7B shows an HPLC separation curve of lactose in the milk sample from a normal ICR mouse, used as the normal control of the experiment in Example 6. FIG. 7C shows an HPLC map of the milk sample from an ecLPH transgenic mouse, showing that 50% of the lactose was degraded to glucose. FIG. 7D shows an HPLC map of the milk sample from a non-transgenic mouse, proving that the milk contained only lactose.

Figure 8:
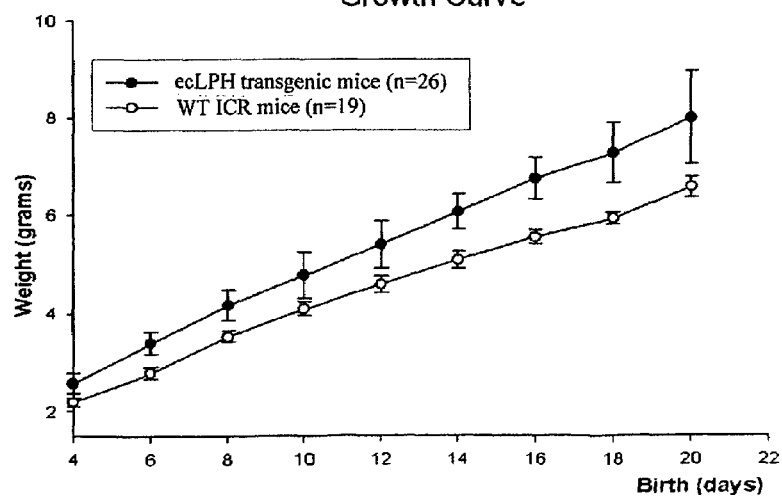

FIG. 8 shows a comparison of the youngling growth curves of ecLPH transgenic mice and normal ICR mice in the lactation period. In each brood of the normal ICR mice and transgenic mice, the subject numbers of the younglings were controlled between 8 to 10. The weights of the younglings of the normal ICR mice and transgenic mice were measured every two days from the $4^{th}$ day after birth. Statistical data showed that the two groups had a significant difference of $p<0.001$ during the $4^{th}$ to $20^{th}$ days after birth.

DETAILED DESCRIPTION OF THE INVENTION

The present invention provides a transgenic animal producing low-lactose milk, wherein the transgenic animal is transformed with a novel gene encoding an extracellular lactase-hydrolyzing enzyme cloned from a human small intestinal cDNA library according to the present invention. According to an embodiment of the present invention, the gene encoding an extracellular human lactase-hydrolyzing enzyme of the present invention is preferably an extracellular human lactase-phlorizin hydrolase gene, more preferably the new extracellular human lactase-phlorizin hydrolase gene of the present invention (ecLPH). The newly identified ecLPH cDNA clone containing a secreting signal peptide in the N-terminus and lacking a transmembrane domain in the C-terminus was verified as encoding a membrane-anchorless extracellular protein in this invention when compared to the known human lactase-phlorizin hydrolase (hLPH) gene. Since the extracellular lactase-hydrolyzing enzyme gene is constructed in a mammary gland-specific expression vector, after being introduced into an animal, the transgene can be continuously and stably expressed during lactation, producing large amounts of proteins with the activity of degrading lactose. The expression of the heterologous gene in tissues of the mammary gland does not affect the normal physiological functions of the transgenic animal. The transgene specific for mammary gland expression even lacks any additional selection gene for antibiotic resistance. Further, mammals transformed by the technology of the present invention breed filial generations carrying the heterologous transgene, with amounts of expression comparable to their transformed parental generation and thus can be used to produce low-lactose milk.

The present invention also provides a method for producing a transgenic animal that produces low-lactose milk, wherein the animal is transformed with a gene encoding an extracellular lactase-hydrolyzing enzyme, preferably an extracellular lactase-phlorizin hydrolase gene, more preferably the extracellular lactase-phlorizin hydrolase gene of the present invention (ecLPH). The newly identified ecLPH cDNA clone containing a secreting signal peptide in the N-terminus and lacking a transmembrane domain in the C-terminus was proposed as a membrane-anchorless extracellular protein in this invention when compared to the known human lactase-phlorizin hydrolase (hLPH) gene. The inventors have clearly demonstrated that the exogenic ecLPH protein can be secreted into the mammary alveolar cavity (FIG. 6B) of lactating transgenic mice. In contrast, the exogenic hLPH protein can only be found in the membrane portion of the mammary gland (FIG. 6A) of lactating transgenic mice.

According to an example of the present invention, the animal was transformed with the heterologous gene expression vector construct of the present invention.

Another embodiment of the present invention also provides a novel extracellular human lactase-phlorizin hydrolase (ecLPH) gene, which was cloned from a human small intestinal cDNA library and can be expressed with a mammary gland-specific expression vector. The ecLPH cDNA of the present invention has a full length of 4.2 kb, and encodes an extracellular protein without a membrane-binding domain. Compared with the gene sequence of the known mature human lactase-phlorizin hydrolase (hLPH) (FIG. 2, top panel), the ecLPH cDNA of the present invention (FIG. 2, bottom panel) lacks Exon 12 and Exon 15-17, which compeletely spliced out the transmembrane domain. The coding region structure of the ecLPH cDNA of the present invention is shown in FIG. 2. The newly identified ecLPH cDNA clone containing a secreting signal peptide in the N-terminus and lacking a transmembrane domain in the C-terminus was verified as a membrane-anchorless extracellular protein in this invention.

According to an embodiment of the present invention, the extracellular human lactase-phlorizin hydrolase gene of the present invention has a nucleotide sequence encoding the amino acid sequence as shown in SEQ ID NO: 2.

According to a preferred embodiment of the present invention, the extracellular human lactase-phlorizin hydrolase gene of the present invention has the nucleotide sequence as shown in SEQ ID NO: 1, or a degenerate sequence or a complementary sequence thereof.

In another embodiment, the present invention relates to a heterologous gene expression vector construct comprising the gene of the present invention that can be expressed with a mammary gland-specific expression vector. More specifically, the construct comprises four parts: (1) a promoter 5'-regulatory sequence, which is specific for expression in the mammary gland epithelial cells and can regulate the heterologous gene so that the gene is continuously and stably expressed during the lactation period of the transgenic mammal; (2) a mammary gland-specific extracellular signal peptide sequence, which can guide the heterologous proteins expressed in the mammary gland epithelial cells of the transgenic mammal so that the proteins are efficiently secreted into the milk; (3) a heterologous gene, which is downstream of and regulated by the 5'-regulatory sequence and the extracellular signal peptide; and (4) a 3'-regulatory sequence, which is downstream of the coding sequence of the heterologous gene, comprising a polyadenylation signal sequence for the stability and integrity of the mRNA molecule transcribed from the heterologous gene and post-transcriptional modification. According to an embodiment of the present invention, the novel extracellular lactase-phlorizin hydrolase (ecLPH) gene of the present invention is constructed downstream of the mammary-gland specific promoter, followed by the polyadenylation signal sequence (0.5 kb) of a bovine growth factor gene to form a mammary gland-specific mammalian vector. The map of the transgene construct is shown in FIG. 3A.

A further embodiment of the present invention relates to a method for producing low-lactose milk, wherein the heterologous gene expression vector construct of the present invention is introduced into a pronucleus to produce a transgenic animal that produces low-lactose milk. According to an example of the present invention, the milk of the transgenic animal showed that the heterologous gene was highly expressed in the mammary gland, and the transgene was continuously and stably expressed during lactation to produce large amounts of proteins with the activity of degrading lactose. This proved that the transgenic animal could indeed be used to produce low-lactose milk.

In addition, it was surprisingly found in the present invention that when transgenic female mice of the present invention mated during the same period with normal ICR female mice and fed their pups with the milk secreted after their pregnancy and delivery, the weights of pups receiving milk from the LPH transgenic mice increased more than those of the normal ICR control group, with a statistically significant difference ($p<0.001$) (shown in FIG. 8). This result not only showed that the novel ecLPH protein had a function of degrading lactose, but also indicated that the transformed monosaccharide components (i.e., glucose and galactose) could be digested more easily and might provide assistance in intestinal digestion and absorption. The result also indicated that the ability to lactate was raised due to a change of the role of lactose in balancing the osmotic pressure. Accordingly, the present invention also provides a method for increasing the growth rate and weight gain of a newborn animal, comprising transforming a maternal animal with the extracellular lactase-phlorizin hydrolase gene of the present invention, and feeding the newborn animal with the milk secreted after pregnancy and delivery of the transformed animal, preferably from the pregnant transgenic animal.

The aforementioned animals refer to mammals, including but not limited to mice, cows, goats and sheep, preferably cows, goats and sheep.

The following examples are provided for further illustrating the present invention, but not for limiting the present invention.

EXAMPLE 1

Screening for a Novel Extracellular Lactase-phlorizin Hydrolase (ecLPH) Gene in a Human Small Intestine 5'-stretch cDNA Library The screening was conducted with small fragments of specific LPH nucleotides in a human small intestine 5'-stretch cDNA library. The small fragments of specific human LPH nucleotides were obtained from the GenBank of NCBI Sequence Viewer (Accession Number: X07994) for the designation of primer sets to generate a probe used in cDNA library screening. The primers used in screening for LPH cDNA are:

```
Primer 1:
5'-CTCTCTTGTCATCCTCTTCC-3';    (SEQ ID NO: 3)

and

Primer 2:
5'-AACAAGTCAATCAAGGCAGG-3'.    (SEQ ID NO: 4)
```

The primers used in screening for ecLPH cDNA are:

```
Primer 3:
5'-CAGACTTTTGTTTCCAGACC-3';    (SEQ ID NO: 5)

Primer 4:
5'-TCAACAACACGAACAGGC-3';      (SEQ ID NO: 6)

and

Primer 5:
5'-ACAGAAATGCCAAGCCACAG-3'.    (SEQ ID NO: 7)
```

In the first round, a total of $5\times10^4$ pfu phages were screened. Developed X-ray films were properly cut and oriented with the phage culture plates to check for hybridization signals on the X-ray films. Only those culture plates with overlapping hybridization signals on the X-ray films developed from two duplicate nitrocellulose (NC) films were selected. A total of five hybridization signal spots were screened out in the first round, designated as 1-1, 4-1, 4-2, 4-3 and 5-1, respectively. The concentrations of the phages were determined by a rapid quantitative method using a serial dilution of phage plating on agar plates, followed by the second and third rounds of screening. The concentrations of the five recombinant phage clones obtained after three rounds of screening were determined by the same rapid quantitative method. The phages were proliferated in 150 mm culture plates to obtain a high-concentration phage liquid. Phage DNA was extracted by phenol/chloroform purification and ethanol precipitation, and the insert fragment was analyzed by restriction digestion (shown in FIG. 1).

The DNA of the five recombinant phage strains was digested with EcoRI to separate the vector from the carried hLPH cDNA fragment, and then analyzed by 0.8% gel electrophoresis. It was found that three of the clones carried the same hLPH cDNA fragment, which was about 6.2 kb, while the other two clones carried a cloned fragment of about 4.2 kb. The two types of clones were designated as 4-1-1-1 and 5-1-2-1, respectively, and were fully sequenced. The results of the sequencing showed that the cloned 6.2 kb hLPH fragment (No. 4-1-1-1) encoded a membrane-anchored protein comprising a membrane-binding domain, while the cloned 4.2 kb ecLPH fragment (No. 5-1-2-1) encoded an extracellular protein comprising no membrane-binding domain, which is the novel ecLPH of the present invention. The gene coding region structure of the novel ecLPH cDNA is shown in FIG. 2. The various colored sections in FIG. 2 of LPH and ecLPH (also called LPH1) mRNA structures are indicated, where present, as a precursor sequence (blue box region), a mature lactase-phlorizin hydrolase domain (red box region), a transmembrane domain (green box region), and a novel 3'-UTR region (yellow box region). The known hLPH cDNA has a full length of 6.2 kb and encodes a membrane-anchored protein comprising a membrane-binding domain, while the newly cloned ecLPH (also called LPH1) cDNA has a full length of 4.2 kb and lacks Exon 12 and Exon 15-17, encoding an extracellular protein comprising no membrane-binding domain.

After sequencing, the genetic sequence was deduced for the ecLPH gene and expressed protein of the present invention. The nucleotide sequence is SEQ ID NO: 1 and the amino acid sequence is SEQ ID NO: 2.

EXAMPLE 2

Production of Transgenic Mice and Dairy Goats Carrying the Lactase-phlorizin Hydrolase (ecLPH) Gene According to the present invention, to breed a transgenic mammal, the extracellular human lactase-phlorizin hydrolase (ecLPH) gene was constructed into a mammary gland-specific alpha-lactalbumin (α-LA) promoter (2.0 kb) by DNA ligation reaction, followed by the polyadenylation signal sequence (0.5 kb) of a bovine growth factor gene (bGH polyA) to form a mammary gland-specific mammal vector. A map of the transgene construct is shown in FIG. 3A. The various colored sections in FIG. 3A of the transgene map indicated a mammary gland-specific α-LA promoter (dark blue box region), a secretion signal peptide (green box region), a mature lactase-phlorizin hydrolase domain (domain III and IV colored by pink box region), and a novel 3'-UTR region (light blue box region). The vector constructed in a plasmid as stated above was amplified by shaking the culture in 500-ml volume of bacterial host cells and purified by plasmid DNA extraction in lysozyme and alkali reagent. A transgene construct of high purity was obtained following a preparation process comprising double digestions of HindIII and XbaI restriction enzymes and CsCl-gradient ultracentrifugation for DNA banding processing. The transgene was mixed at a concentration of 1-2 ng/µl into a suitable microinjection buffer (10 mM Tris-HCl, 0.1 mM EDTA; pH 7.4), and injected into a male pronucleus of =mammal one-cell stage embryos by the microinjection technique. The embryos were then transferred into the uterus of a female mammal. For the animal subjects born after pregnancy, rapid PCR screening and Southern blotting were performed on their tissue DNA to analyze the insertion pattern of the heterologous transgene in the animal genome. The results are shown in FIG. 3B and FIG. 3C. One strain of transgenic dairy goats and 7 strains of transgenic mice were obtained by this method.

The nucleotide sequencing analysis showed that there was only one BamHI restriction site located near the 3'-end of the ecLPH transgene (FIG. 3A). Therefore, the insertion and possible concatamerizing patterns of the LPH transgene in the chromosomes of each mouse were determined by Southern blot hybridization. Based on the resulting signals, it was determined that the heterologous gene was inserted in the mouse genome with various concatamerizing patterns. The concatamerizing patterns of the heterologous gene included head-to-head, tail-to-tail and head-to-tail concatamerization. Moreover, the heterologous genes in parental transgenic mice No. 1 and No. 3 were passed to their offspring without difference in the concatamerizing pattern (left blot in FIG. 3B). As for parental transgenic mouse No. 5, the heterologous gene existed in the genome of its offspring mostly in a concatamerizing pattern wherein 5.5 kb was missing, except that No. 102 received the complete heterologous gene (right blot in FIG. 3B). These results showed that the heterologous genes in all of the three strains could be completely passed through the germ-line transmission.

EXAMPLE 3

Quantitative Analysis of Milk of the Transgenic Female Mice

Milk samples of the transgenic female mice of Example 2 were collected for quantitative analysis. A glass pipette sealed by mineral oil was used to collect milk samples. Milk was drawn from anesthetized transgenic female mice, which were treated with oxytocin, by squeezing massage. Milk samples were collected on the $7^{th}$ and $14^{th}$ days. The milk of No. 1 ($F_0$; female) and No. 3 ($F_0$; female) of the parental generation, and that of No. 136 and No. 137 of the filial generation (offspring of No. 5 ($F_0$; male)) were sampled during their lactation. Since mouse milk contains large amounts of casein and lipid, the collected milk samples were first diluted 20-fold with deionized water, and then centrifuged at 3,000 rpm for 10 minutes at 4° C. The whey portion was taken so that the lipid would not interfere with the gel electrophoresis of proteins. The partially purified milk was subjected to polyacrylamide gel electrophoresis (12% SDS-PAGE) for 1.5 hours running time under 100 volts and stained with Coomassie blue. The proteins on the electrophoresis gel were transferred to a PVDF cellulose membrane to perform Western blotting. A rabbit anti-LPH antibody was used to examine the amount of ecLPH proteins in the skim milk of transgenic mice by Western blot hybridization and ELISA assays. The result showed that a specific signal appeared at a molecular weight of 66 kD. The signal was not observed in normal ICR mice of the same strain. Therefore, the exogenic human ecLPH protein was indeed expressed in the mammary gland and secreted in the milk of transgenic animals (FIG. 4). Using β-casein as an internal control to obtain a quantitative calibrated value, it was determined that the amount of the exogenic human ecLPH protein in the milk of transgenic mice at the $14^{th}$ day of the lactating period was much higher than that in the milk of the $7^{th}$ day. The highest amount of the exogenic human ecLPH protein detected from the milk of the transgenic animals was 780 µg/ml. It was clearly demonstrated that the newly cloned ecLPH gene encoded an extracellular secreting ecLPH protein.

EXAMPLE 4

Figure 5:
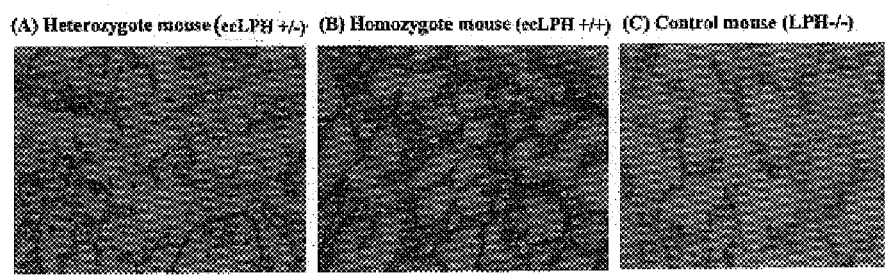

Immuno-histochemistry Staining Analysis of Mammary-gland Tissue Sections of the Transgenic Female Mice To examine the difference in the expression level of the exogenic human ecLPH protein between homozygous $F_3$ offspring subjects (ecLPH+/+) and heterozygous $F_3$ offspring subjects (ecLPH+/−), the transgenic female mice produced according to the method of Example 2 were sacrificed during their lactation period, and their mammary gland tissues were taken for freeze embedding sectioning and immuno-histochemistry staining (IHC). It was clearly observed from the staining that there were red signals resulting from AEC chromogens (peroxidase substrate) degraded by HRP (horseradish peroxidase) enzymes bound on the secondary antibodies, representing target proteins in the mammary glands of the transgenic mice, which were recognized by the specific monoclonal antibodies. Treated by the same IHC conditions, no equivalent signal was observed in the mice of the normal ICR control group (FIG. 5). Therefore, it was determined that the target protein was indeed expressed in the mammary glands of the transgenic mice, and that homozygous transgenic female mice had higher expression than heterozygous ones. As for the location of expression in mammary-gland tissues, signals clearly appeared in the epithelia, alvoli cavities and lactiferous tubules. This result directly indicated that the exogenic human ecLPH protein pertains to the extracellular form.

EXAMPLE 5

X-Fuc Activity Staining Analysis of Mammary Gland Tissue Sections of the ecLPH Transgenic Female Mice To further examine the physiological enzyme activity of the ecLPH proteins in the milk of the transgenic animals, both transgenic female mice and normal ICR female mice were sacrificed on the $14^{th}$ day of their lactation period, and their mammary-gland tissues were taken for freeze embedding sectioning and activity staining with an LPH-specific X-Fuc chromogen substrate. The chromogen substrate is an analog of 5-bromo-4-chloro-3-indolyl β-D-galactoside (X-gal), differing in that X-Fuc is specifically degraded by the lactase-phlorizin hydrolase domain of LPH enzyme to produce a signal of a blue degraded product. The tissues were fixed on slides with 4% paraformaldehyde in room temperature for 30 minutes and washed 3 times with phosphate buffered saline (PBS). The slides with cells attached and fixed thereon were covered with 1 mM X-Fuc (the lactase-specific chromogen substrate) dissolved in 1 M maleate buffer (pH6.5) containing 0.5 mM p-chloromercuribenzoate, 0.05 M potassium ferricyanide and 0.05 M potassium ferrocyanide, and carefully put in a chamber with sufficient moisture. The slides were left overnight at 37° C. for reaction, and excessive fluid resulting from the reaction was removed. The slides were washed twice with PBS, covered with 80% glycerin and sealed. The slides were observed under a microscope for coloration, and photographed with a digital camera for recording. In FIG. 6B, blue signals resulting from degradation of the X-Fuc substrate clearly appeared in the alveoli cavity of the mammary gland of the ecLPH transgenic mice, while no blue signal was generated at the same location of the control group of normal ICR female mice (FIG. 6C). In contrast, we also generated a control transgenic mice harboring the prior art membrane-anchored LPH gene in the same mammary expression vector to compare their protein localization and enzyme activity in the mammary gland. The blue stain of degradation of X-Fuc substrate was only presented near the epithelial layer in the mammary gland of the LPH transgenic mice as shown in FIG. 6A.

EXAMPLE 6

Examination of Lactose-degrading Ability of ecLPH Enzymes in the Milk of the Transgenic Animals It was determined from the results obtained in the previous examples that ecLPH could be highly expressed in the mammary gland, and the activity thereof has been proved with X-Fuc. However, direct evidence proving the degradation ability of ecLPH is still required for confirming if ecLPH can completely decompose the lactose in milk. When lactose is decomposed, two monosaccharide molecules, galactose and glucose, are generated. Therefore, except for directly proving the degradation of lactose, detecting the increase in the amounts of galactose and glucose can also be utilized to confirm if the heterologous hLPH1 resulting from the expression of the ecLPH gene can decompose lactose, the major disaccharide molecule in milk. In the present invention, standard samples of glucose, the monosaccharide molecule and lactose, the disaccharide molecule were established by HPLC analysis for comparison with the test samples (FIG. 7A). In the HPLC separation curve of the milk sample from a normal ICR mouse (FIG. 7B), only the peak of lactose appeared, which was used as the control of normal mouse milk in the present experiment. In the HPLC map of the milk sample from the ecLPH transgenic mouse (FIG. 7C), the peaks of both lactose and glucose clearly appeared. This result showed that 50% of the lactose was degraded into glucose. As for the HPLC map of the milk sample from a non-transgenic mouse (FIG. 7D), only one peak appeared, proving that the milk contains only lactose, the same as that of the normal ICR mouse.

EXAMPLE 7

Comparison of the Growth Curves of ecLPH Transgenic Mice and Normal ICR Mice Transgenic female mice and normal ICR female mice were bred at the same time. The $4^{th}$ day after the delivery was the first day of measuring the weights of the filial mice. Afterwards, the weight of each of the filial mice was measured every two days. The results of the weights measured on the $4^{th}$ day and thereafter showed that the filial mice receiving milk from these LPH transgenic mice of the present invention (n=26) increased more than the weight of the normal ICR control group (n=19), with a statistically significant difference of $p<0.001$ (shown in FIG. 8). Such results not only showed that the novel ecLPH protein had a function of degrading lactose, but also suggested that the transformed monosaccharide components (i.e., glucose and galactose) could be digested more easily and might provide assistance in intestinal digestion and absorption. The results showed that the ecLPH-containing milk can increase the growth rate and weight gain of newborn animals by predigestion of lactose in their nursing milk.

The present invention successfully cloned the novel extracellular lactase-phlorizin hydrolase (ecLPH) gene, and transformed mammals like dairy goats and mice with the human ecLPH gene. The transgene can be continuously and stably expressed during lactation, producing large amounts of proteins having the activity of degrading lactose. The expression of the heterologous gene in tissues of the mammary gland does not affect the normal physiological functions of the transgenic animal. The transgene specific for mammary gland expression even lacks any additional selection gene for antibiotic resistance. Further, mammals transformed by the technology of the present invention breed filial generations carrying the heterologous transgene, with amounts of expression comparable to their transformed parental generation and thus can be used to produce low-lactose milk.

Without departing from the spirit and scope of the present invention, in view of the present disclosure, anyone skilled in the art may make various changes and modifications to introduce different heterologous genes, which falls within the protected scope of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A non-human transgenic mammal, wherein the transgenic mammal has a genome comprising a mammary gland-specific promoter operably linked to a polynucleotide sequence consisting of SEQ ID NO:1 encoding an extracellular lactase-hydrolyzing enzyme having the amino acid sequence of SEQ ID NO:2, wherein the transgenic mammal is capable of producing milk comprising the extracellular lactase-hydrolyzing enzyme.

2. The non-human transgenic mammal according to claim 1, wherein the mammal is selected from the group consisting of a mouse, a cow, a goat and a sheep.

3. The non-human transgenic mammal according to claim 2, wherein the mammal is a cow.

4. The non-human transgenic mammal according to claim 2, wherein the mammal is a goat.

5. The non-human transgenic mammal according to claim 2, wherein the mammal is a sheep.

6. A method for producing low-lactose milk, comprising providing the non-human transgenic mammal of any one of claims 1, 2, 3, 4 and 5, and obtaining the low-lactose milk from the transgenic animal.

7. A method for producing a non-human transgenic mammal that produces low-lactose milk, comprising providing a milk-producing mammal and transferring into the uterus of the mammal a one-cell stage embryo microinjected with a polynucleotide comprising a mammary gland-specific promoter operably linked to a polynucleotide sequence consisting of SEQ ID NO:1 encoding an extracellular lactase-hydrolyzing enzyme having the amino acid sequence of SEQ ID NO:2, wherein the transgenic female offspring of the mammal is capable of producing low-lactose milk comprising the extracellular lactase-hydrolyzing enzyme.

8. A method for increasing the growth rate and weight gain of a newborn mammal, comprising providing a female milk-producing transgenic non-human mammal of any one of claims 1, 2, 3, 4 and 5, and feeding the newborn mammal with milk secreted by the transgenic maternal mammal after delivery of the newborn mammal.

9. The method of claim 8, wherein the newborn mammal is a mammal delivered from the transgenic mammal following the pregnancy of the transgenic mammal.

* * * * *

SEQUENCE LISTING

<160> NUMBER OF SEQ ID NOS: 7

<210> SEQ ID NO 1
<211> LENGTH: 3246
<212> TYPE: DNA
<213> ORGANISM: Homo sapiens -continued

```
<400> SEQUENCE: 1
atgaaacttc tcatccttac ctgtcttgtg gctgttgctg ccaggttaac cctcccctcc      60
aaagtcagag ccttcacttt tccatctgag gtgccctcca aggctaaagt cgtttgggaa     120
aagttctcca gccaacccaa gttcgaaaga gatttgttct accacgggac gtttcgggat     180
gactttctgt ggggcgtgtc ctcttccgct tatcagattg aaggcgcgtg ggatgccgat     240
ggcaaaggcc ccagcatctg gataactttt acccacacac cagggagcaa tgtgaaagac     300
aatgccactg gagacatcgc ctgtgacagc tatcaccagc tggatgccga tctgaatatg     360
ctccgagctt gaaggtgaa ggcctaccgc ttctctatct cctggtctcg gattttccca      420
actgggagaa acagctctat caacagtcat ggggttgatt attacaacag gctgatcaat     480
ggcttggtgg caagcaacat ctttcccatg gtgacattgt tccattggga cctgccccag     540
gccctccagg atatcggagg ctgggagaat cctgccttga ttgacttgtt tgacagctac     600
gcagactttt gtttccagac ctttggtgat agagtcaagt tttggatgac ttttaatgag     660
cccatgtacc tggcatggct aggttatggc tcagggaat tccccccagg ggtgaaggac      720
ccaggctggg caccatatag gatagcccac gccgtcatca aagcccatgc cagagtctat     780
cacacgtacg atgagaaata caggcaggag cagaaggggg tcatctcgct gagcctcagt     840
acacactggg cagagcccaa gtcaccaggg gtccccagag atgtggaagc cgctgaccga     900
atgctgcagt tctccctggg ctggtttgct cacccccattt ttagaaacgg agactatcct    960
gacaccatga gtggaaagt gggaacagg agtgaactgc agcacttagc cacctcccgc      1020
ctgccaagct tcactgagga agagaagagg ttcatcaggg cgacggccga cgtcttctgc    1080
ctcaacacgt actactccag aatcgtgcag cacaaaacac ccaggctaaa cccacccctcc   1140 tacgaagacg accaggagat ggctgaggag gaggacccct cgtggccttc cacggcaatg    1200
aacagagctg cgccctgggg gacgcgaagg ctgctgaact ggatcaagga agagtatggt    1260
gacatcccca tttacatcac cgaaaacgga gtggggctga ccaatccgaa cacggaggat    1320
actgatagga tatttttacca caaaacctac atcaatgagg cttttgaaagc ctacaggctc   1380 gatggtatag accttcgagg gtatgtcgcc tggtctctga tggacaactt tgagtggcta    1440
aatggctaca cggtcaagtt tggactgtac catgttgatt tcaacaacac gaacaggcct    1500
cgcacagcaa gagcctccgc caggtactac acagaggtca ttaccaacaa cggcatgcca    1560
ctggccaggg aggatgagtt tctgtacgga cggtttcctg agggcttcat ctggagtgca    1620
gcttctgctg catatcagat tgaaggtgcg tggagagcag atggcaaagg actcagcatt    1680
tgggacacgt tttctcacac accactgagg gttgagaacg atgccattgg agacgtggcc    1740
tgtgacagtt atcacaagat tgctgaggat ctggtcaccc tgcagaacct gggtgtgtcc    1800
cactaccgtt tttccatctc ctggtctcgc atcctccctg atggaaccac caggtacatc    1860
aatgaagcgc gcctgaacta ctacgtgagg ctcatcgata cactgctggc cgccagcatc    1920
cagccccagg tgaccattta ccactgggac ctaccacaga cgctccaaga tgtaggaggc    1980
tgggagaatg agaccatcgt gcagcggttt aaggagtatg cagatgtgct cttccagagg    2040
ctgggagaca aggtgaagtt ttggatcacg ttgaatgagc cctttgtcat tgcttaccag    2100
ggctatggct acggaacagc agctccagga gtctccaata ggcctggcac tgcccctac    2160 attgttggcc acaatctaat aaaggctcat gctgaggcct ggcatctgta caacgatgtg    2220
taccgcgcca gtcaaggtgg cgtgatttcc atcaccatca gcagtgactg gctgaacccc    2280
agagatccct ctaaccagga ggatgtggag gcagccagga gatatgttca gttcatggga    2340
```

-continued

```
ggctggtttg cacatcctat tttcaagaat ggagattaca atgaggtgat gaagacgcgg   2400
atccgtgaca ggagcttggc tgcaggcctc aacaagtctc ggctgccaga atttacagag   2460
agtgagaaga ggaggatcaa cggcacctat gactttttg ggttcaatca ctacaccact    2520
gtcctcgcct acaacctcaa ctatgccact gccatctctt cttttgatgc agacagagga   2580
gttgcttcca tcgcagatcg ctcgtggcca gactctggct ccttctggct gaagatgacg   2640
ccttttggct tcaggaggat cctgaactgg ttaaaggagg aatacaatga ccctccaatt   2700
tatgtcacag agaatggagt gtcccagcgg aagaaacag acctcaatga cactgcaagg    2760
atctactacc ttcggactta catcaatgag gccctcaaag ctgtgcagga caaggtggac   2820
cttcgaggat acacagtttg gagtgcgata gacaatttg agtgggccac aggcttttca    2880
gagagatttg gtctgcattt tgtgaactac agtgacccctt ctctgccaag gatcccaaa   2940 gcatcagcga agttctacgc ctctgtggtc cgatgcaatg gcttccctga ccccgctaca   3000
gggcctcacg cttgtctcca ccagccagat gccggaccca ccatcagccc cgtgagacag   3060
gaggaggtgc agttcctggg gctaatgctc ggcatcacag aagcacagac agctttgtac   3120
gttctctttt ctcttgtgct tcttggagtc tgtggcttgg catttctgtc atacaagtac   3180
tgcaagcgct ctaagcaagg gaaaacacaa cgaagccaac aggaattgag cccggtgtct   3240
tcattc                                                               3246
```

<210> SEQ ID NO 2
<211> LENGTH: 1082
<212> TYPE: PRT
<213> ORGANISM: Homo sapiens

<400> SEQUENCE: 2

```
Met Lys Leu Leu Ile Leu Thr Cys Leu Val Ala Val Ala Ala Arg Leu
1               5                   10                  15

Thr Leu Pro Ser Lys Val Arg Ala Phe Thr Phe Pro Ser Glu Val Pro
            20                  25                  30

Ser Lys Ala Lys Val Val Trp Glu Lys Phe Ser Ser Gln Pro Lys Phe
        35                  40                  45

Glu Arg Asp Leu Phe Tyr His Gly Thr Phe Arg Asp Asp Phe Leu Trp
    50                  55                  60

Gly Val Ser Ser Ser Ala Tyr Gln Ile Glu Gly Ala Trp Asp Ala Asp
65                  70                  75                  80

Gly Lys Gly Pro Ser Ile Trp Asp Asn Phe Thr His Thr Pro Gly Ser
                85                  90                  95

Asn Val Lys Asp Asn Ala Thr Gly Asp Ile Ala Cys Asp Ser Tyr His
            100                 105                 110

Gln Leu Asp Ala Asp Leu Asn Met Leu Arg Ala Leu Lys Val Lys Ala
        115                 120                 125

Tyr Arg Phe Ser Ile Ser Trp Ser Arg Ile Phe Pro Thr Gly Arg Asn
    130                 135                 140

Ser Ser Ile Asn Ser His Gly Val Asp Tyr Tyr Asn Arg Leu Ile Asn
145                 150                 155                 160

Gly Leu Val Ala Ser Asn Ile Phe Pro Met Val Thr Leu Phe His Trp
                165                 170                 175

Asp Leu Pro Gln Ala Leu Gln Asp Ile Gly Gly Trp Glu Asn Pro Ala
            180                 185                 190

Leu Ile Asp Leu Phe Asp Ser Tyr Ala Asp Phe Cys Phe Gln Thr Phe
        195                 200                 205
```

```
Gly Asp Arg Val Lys Phe Trp Met Thr Phe Asn Glu Pro Met Tyr Leu
    210                 215                 220

Ala Trp Leu Gly Tyr Gly Ser Gly Glu Phe Pro Pro Gly Val Lys Asp
225                 230                 235                 240

Pro Gly Trp Ala Pro Tyr Arg Ile Ala His Ala Val Ile Lys Ala His
                245                 250                 255

Ala Arg Val Tyr His Thr Tyr Asp Glu Lys Tyr Arg Gln Glu Gln Lys
            260                 265                 270

Gly Val Ile Ser Leu Ser Leu Ser Thr His Trp Ala Glu Pro Lys Ser
        275                 280                 285

Pro Gly Val Pro Arg Asp Val Glu Ala Ala Asp Arg Met Leu Gln Phe
    290                 295                 300

Ser Leu Gly Trp Phe Ala His Pro Ile Phe Arg Asn Gly Asp Tyr Pro
305                 310                 315                 320

Asp Thr Met Lys Trp Lys Val Gly Asn Arg Ser Glu Leu Gln His Leu
                325                 330                 335

Ala Thr Ser Arg Leu Pro Ser Phe Thr Glu Glu Lys Arg Phe Ile
            340                 345                 350

Arg Ala Thr Ala Asp Val Phe Cys Leu Asn Thr Tyr Tyr Ser Arg Ile
        355                 360                 365

Val Gln His Lys Thr Pro Arg Leu Asn Pro Pro Ser Tyr Glu Asp Asp
370                 375                 380

Gln Glu Met Ala Glu Glu Asp Pro Ser Trp Pro Ser Thr Ala Met
385                 390                 395                 400

Asn Arg Ala Ala Pro Trp Gly Thr Arg Arg Leu Leu Asn Trp Ile Lys
                405                 410                 415

Glu Glu Tyr Gly Asp Ile Pro Ile Tyr Ile Thr Glu Asn Gly Val Gly
            420                 425                 430

Leu Thr Asn Pro Asn Thr Glu Asp Thr Asp Arg Ile Phe Tyr His Lys
        435                 440                 445

Thr Tyr Ile Asn Glu Ala Leu Lys Ala Tyr Arg Leu Asp Gly Ile Asp
    450                 455                 460

Leu Arg Gly Tyr Val Ala Trp Ser Leu Met Asp Asn Phe Glu Trp Leu
465                 470                 475                 480

Asn Gly Tyr Thr Val Lys Phe Gly Leu Tyr His Val Asp Phe Asn Asn
                485                 490                 495

Thr Asn Arg Pro Arg Thr Ala Arg Ala Ser Ala Arg Tyr Tyr Thr Glu
            500                 505                 510

Val Ile Thr Asn Asn Gly Met Pro Leu Ala Arg Glu Asp Glu Phe Leu
        515                 520                 525

Tyr Gly Arg Phe Pro Glu Gly Phe Ile Trp Ser Ala Ala Ser Ala Ala
    530                 535                 540

Tyr Gln Ile Glu Gly Ala Trp Arg Ala Asp Gly Lys Gly Leu Ser Ile
545                 550                 555                 560

Trp Asp Thr Phe Ser His Thr Pro Leu Arg Val Glu Asn Asp Ala Ile
                565                 570                 575

Gly Asp Val Ala Cys Asp Ser Tyr His Lys Ile Ala Glu Asp Leu Val
            580                 585                 590

Thr Leu Gln Asn Leu Gly Val Ser His Tyr Arg Phe Ser Ile Ser Trp
        595                 600                 605

Ser Arg Ile Leu Pro Asp Gly Thr Thr Arg Tyr Ile Asn Glu Ala Gly
    610                 615                 620
```

-continued

```
Leu Asn Tyr Tyr Val Arg Leu Ile Asp Thr Leu Leu Ala Ala Ser Ile
625                 630                 635                 640

Gln Pro Gln Val Thr Ile Tyr His Trp Asp Leu Pro Gln Thr Leu Gln
            645                 650                 655

Asp Val Gly Gly Trp Glu Asn Glu Thr Ile Val Gln Arg Phe Lys Glu
                660                 665                 670

Tyr Ala Asp Val Leu Phe Gln Arg Leu Gly Asp Lys Val Lys Phe Trp
            675                 680                 685

Ile Thr Leu Asn Glu Pro Phe Val Ile Ala Tyr Gln Gly Tyr Gly Tyr
        690                 695                 700

Gly Thr Ala Ala Pro Gly Val Ser Asn Arg Pro Gly Thr Ala Pro Tyr
705                 710                 715                 720

Ile Val Gly His Asn Leu Ile Lys Ala His Ala Glu Ala Trp His Leu
                725                 730                 735

Tyr Asn Asp Val Tyr Arg Ala Ser Gln Gly Gly Val Ile Ser Ile Thr
            740                 745                 750

Ile Ser Ser Asp Trp Ala Glu Pro Arg Asp Pro Ser Asn Gln Glu Asp
        755                 760                 765

Val Glu Ala Ala Arg Arg Tyr Val Gln Phe Met Gly Gly Trp Phe Ala
770                 775                 780

His Pro Ile Phe Lys Asn Gly Asp Tyr Asn Glu Val Met Lys Thr Arg
785                 790                 795                 800

Ile Arg Asp Arg Ser Leu Ala Ala Gly Leu Asn Lys Ser Arg Leu Pro
                805                 810                 815

Glu Phe Thr Glu Ser Glu Lys Arg Arg Ile Asn Gly Thr Tyr Asp Phe
            820                 825                 830

Phe Gly Phe Asn His Tyr Thr Thr Val Leu Ala Tyr Asn Leu Asn Tyr
        835                 840                 845

Ala Thr Ala Ile Ser Ser Phe Asp Ala Asp Arg Gly Val Ala Ser Ile
850                 855                 860

Ala Asp Arg Ser Trp Pro Asp Ser Gly Ser Phe Trp Leu Lys Met Thr
865                 870                 875                 880

Pro Phe Gly Phe Arg Arg Ile Leu Asn Trp Leu Lys Glu Glu Tyr Asn
                885                 890                 895

Asp Pro Pro Ile Tyr Val Thr Glu Asn Gly Val Ser Gln Arg Glu Glu
            900                 905                 910

Thr Asp Leu Asn Asp Thr Ala Arg Ile Tyr Tyr Leu Arg Thr Tyr Ile
        915                 920                 925

Asn Glu Ala Leu Lys Ala Val Gln Asp Lys Val Asp Leu Arg Gly Tyr
930                 935                 940

Thr Val Trp Ser Ala Ile Asp Asn Phe Glu Trp Ala Thr Gly Phe Ser
945                 950                 955                 960

Glu Arg Phe Gly Leu His Phe Val Asn Tyr Ser Asp Pro Ser Leu Pro
                965                 970                 975

Arg Ile Pro Lys Ala Ser Ala Lys Phe Tyr Ala Ser Val Val Arg Cys
            980                 985                 990

Asn Gly Phe Pro Asp Pro Ala Thr  Gly Pro His Ala Cys  Leu His Gln
        995                 1000                 1005

Pro Asp  Ala Gly Pro Thr Ile  Ser Pro Val Arg Gln  Glu Glu Val
    1010                 1015                 1020

Gln Phe  Leu Gly Leu Met Leu  Gly Ile Thr Glu Ala  Gln Thr Ala
    1025                 1030                 1035
```

```
Leu Tyr Val Leu Phe Ser Leu Val Leu Gly Val Cys Gly Leu
    1040            1045                1050

Ala Phe Leu Ser Tyr Lys Cys Lys Arg Ser Lys Gln Gly Lys
    1055            1060                1065

Thr Gln Arg Ser Gln Gln Glu Leu Ser Pro Val Ser Ser Phe
    1070            1075                1080

<210> SEQ ID NO 3
<211> LENGTH: 20
<212> TYPE: DNA
<213> ORGANISM: Artificial
<220> FEATURE:
<223> OTHER INFORMATION: Primer 1

<400> SEQUENCE: 3
ctctcttgtc atcctcttcc                                                 20

<210> SEQ ID NO 4
<211> LENGTH: 20
<212> TYPE: DNA
<213> ORGANISM: Artificial
<220> FEATURE:
<223> OTHER INFORMATION: Primer 2

<400> SEQUENCE: 4
aacaagtcaa tcaaggcagg                                                 20

<210> SEQ ID NO 5
<211> LENGTH: 20
<212> TYPE: DNA
<213> ORGANISM: Artificial
<220> FEATURE:
<223> OTHER INFORMATION: Primer 3

<400> SEQUENCE: 5
cagacttttg tttccagacc                                                 20

<210> SEQ ID NO 6
<211> LENGTH: 18
<212> TYPE: DNA
<213> ORGANISM: Artificial
<220> FEATURE:
<223> OTHER INFORMATION: Primer 4

<400> SEQUENCE: 6
tcaacaacac gaacaggc                                                   18

<210> SEQ ID NO 7
<211> LENGTH: 20
<212> TYPE: DNA
<213> ORGANISM: Artificial
<220> FEATURE:
<223> OTHER INFORMATION: Primer 5

<400> SEQUENCE: 7
acagaaatgc caagccacag                                                 20
```